United States Patent
Sun et al.

(10) Patent No.: US 7,656,523 B2
(45) Date of Patent: Feb. 2, 2010

(54) MULTIPLEXED RAMAN DETECTION WITH FILTER SET

(75) Inventors: Lei Sun, Santa Clara, CA (US);
Tae-Woong Koo, Cupertino, CA (US);
Liming Wang, Sunnyvale, CA (US)

(73) Assignee: Intel Corporation, Santa Clara, CA (US)

( * ) Notice: Subject to any disclaimer, the term of this patent is extended or adjusted under 35 U.S.C. 154(b) by 105 days.

(21) Appl. No.: 11/477,379

(22) Filed: Jun. 30, 2006

(65) Prior Publication Data
US 2008/0002198 A1    Jan. 3, 2008

(51) Int. Cl.
*G01J 3/44* (2006.01)
(52) U.S. Cl. ...................... 356/301; 356/302
(58) Field of Classification Search .............. 356/301
See application file for complete search history.

(56) References Cited

U.S. PATENT DOCUMENTS

| 5,376,556 | A |   | 12/1994 | Tarcha et al. |
| 5,567,628 | A |   | 10/1996 | Tarcha et al. |
| 5,689,333 | A | * | 11/1997 | Batchelder et al. .......... 356/301 |
| 6,614,730 | B1 |   | 9/2003 | Vo-Dinh |
| 6,707,548 | B2 |   | 3/2004 | Kreimer et al. |
| 2003/0059820 | A1 |   | 3/2003 | Vo-Dinh |
| 2006/0046313 | A1 |   | 3/2006 | Roth et al. |

* cited by examiner

*Primary Examiner*—L. G Lauchman
(74) *Attorney, Agent, or Firm*—Pittsbury Winthrop Shaw Pittman LLP

(57) ABSTRACT

A device (and methods of using and manufacturing the device) that utilize a plurality of photomultipliers (PMT)s or a photodiodes coupled with a set of filters to collect Raman signal from samples. Also a method of detecting Raman signals includes receiving Raman signals from a sample utilizing a plurality of photomultiplier tubes (PMT)s or photodiodes, wherein at least one PMT or photodiode provides a different Raman signal than at least one other PMT or photodiode.

37 Claims, 7 Drawing Sheets

FIG. 4a: Sandwich assay with COIN
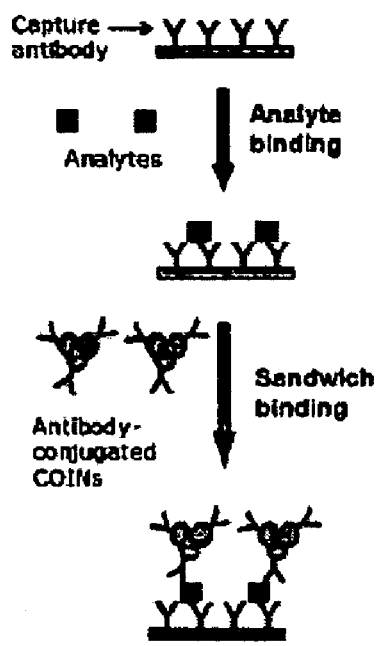
FIG. 4b: COIN's Raman signal quantified by Raman scanning
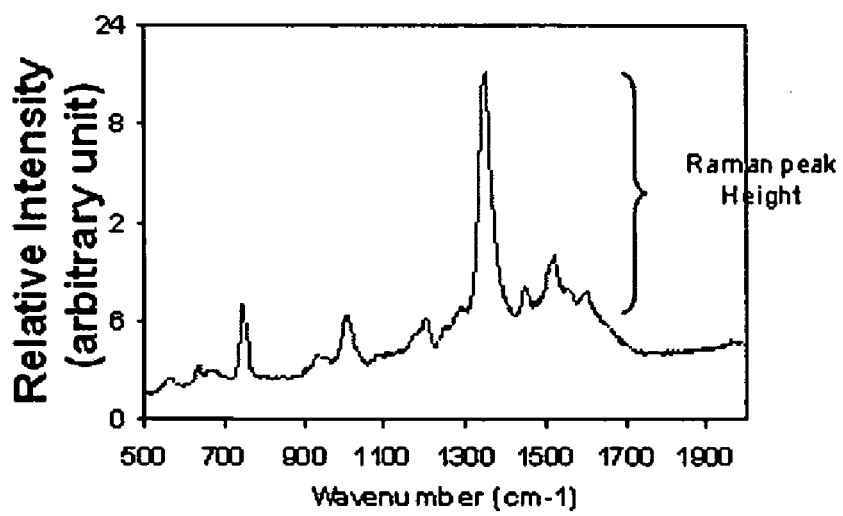

FIG. 4c: COIN's Raman signal quantified by filter-PMT
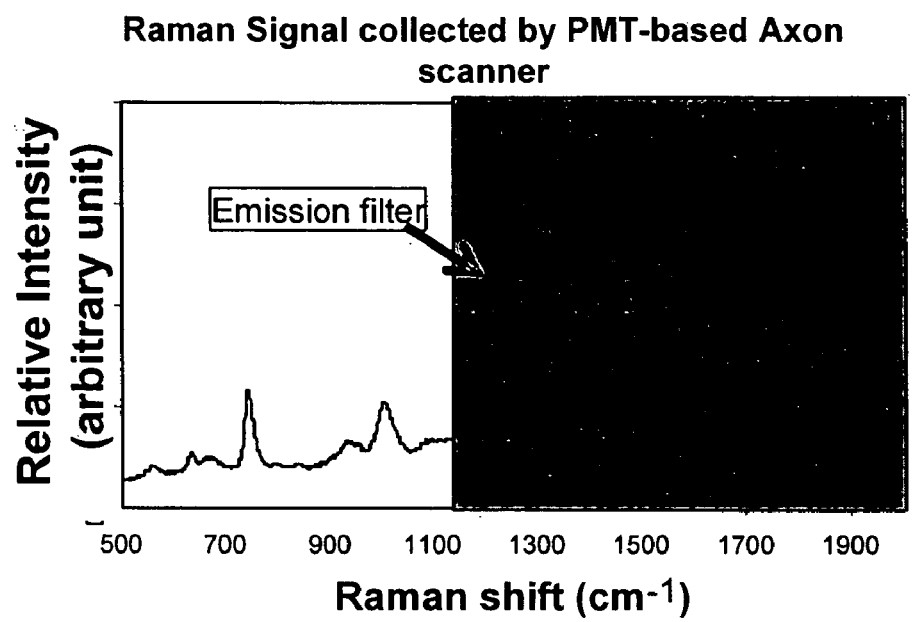
FIG. 4d
IL8 (interleukin 8) sandwich assay performed using COIN Raman label, scanned by PMT-based Axon scanner
Analyte (IL8) concentration increases COIN slide scanned with 532 nm laser → Analyte conc. increases COIN slide scanned with 635 nm laser

MULTIPLEXED RAMAN DETECTION WITH FILTER SET

FIELD OF INVENTION

The embodiments of the invention relate methods and apparatus that utilize a photomultiplier (PMT) set, a photodiode set, or a photodiode array, coupled with a set of filters to collect Raman signal from samples. The invention transcends several scientific disciplines such as polymer chemistry, biochemistry, molecular biology, medicine and medical diagnostics.

BACKGROUND

The ability to detect and identify trace quantities of analytes has become increasingly important in virtually every scientific discipline, ranging from part per billion analyses of pollutants in sub-surface water to analysis of cancer treatment drugs in blood serum. Raman spectroscopy is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed (the analyte). In the practice of Raman spectroscopy, the beam from a light source, generally a laser, is focused upon the sample to thereby generate inelastically scattered radiation, which is optically collected and directed into a wavelength-dispersive spectrometer in which a detector converts the energy of impinging photons to electrical signal intensity.

Among many analytical techniques that can be used for chemical structure analysis, Raman spectroscopy is attractive for its capability to provide rich structure information from a small optically-focused area or detection cavity. Compared to a fluorescent spectrum that normally has a single peak with half peak width of tens of nanometers to hundreds of nanometers, a Raman spectrum has multiple bonding-structure-related peaks with half peak width of as small as a few nanometers.

Typically, the Raman signatures of a sample have been obtained using a spectrometer as shown in FIG. 1. A Raman spectroscopy apparatus typically includes a light source, a spectrometer, and a detector. A typical light source for Raman spectroscopy is a laser. The laser beam can be directed toward the sample to produce Raman scattering, which is a form of non-elastic scattering of incoming photons by molecules within the sample. The Raman scattered light is directed toward a spectrograph which allows the analysis of the wavelength components of the incoming light. Typically, a dispersive spectrometer (such as a Czerny-Turner spectrometer) or a Fourier-transform spectrometer can be used. The spectrometer is connected to a detector, for example, a charge-coupled-device, which converts the incoming photons to electrons. The converted electrons can be read out by an electrical circuit for further storage, display, or analysis.

Other components can be used to improve the performance of the Raman spectroscopy apparatus. For example, a laser line filter (LF) can be used to block light generated by the laser except for the light at the desired wavelength. A dichroic mirror (DM) can be used to separate the excitation light and the Raman scattered light. The dichroic mirror either reflects the laser beam and transmits the Raman scattered light, or transmits the laser beam and reflects the Raman scattered light (the configuration in FIG. 1 is an example of the former). A microscope objective (MO) focuses the laser beam to allow excitation of a small region of the sample, and improves the collection of the Raman scattered light. The sample (S) can be placed on a stage for positioning. A bandpass filter (BF) can be used to block the laser beam from entering the spectrograph. Finally, mirrors (shown as a line) can be used to steer the laser beam or the Raman scattered light.

A spectrometer provides the Raman spectrum of a sample all across a given wavelength.

BRIEF DESCRIPTION OF THE DRAWINGS

FIG. 4a illustrates an embodiment of how sandwich assays can be employed with COINs.

FIG. 4b shows a COIN's Raman signal quantified by Raman scanning.

FIG. 4c shows an embodiment of selectively collecting optical signals from a Raman peak by applying an emission filter.

FIG. 4d shows the raw signal from an Axon scanner.

DETAILED DESCRIPTION

Figure 1:
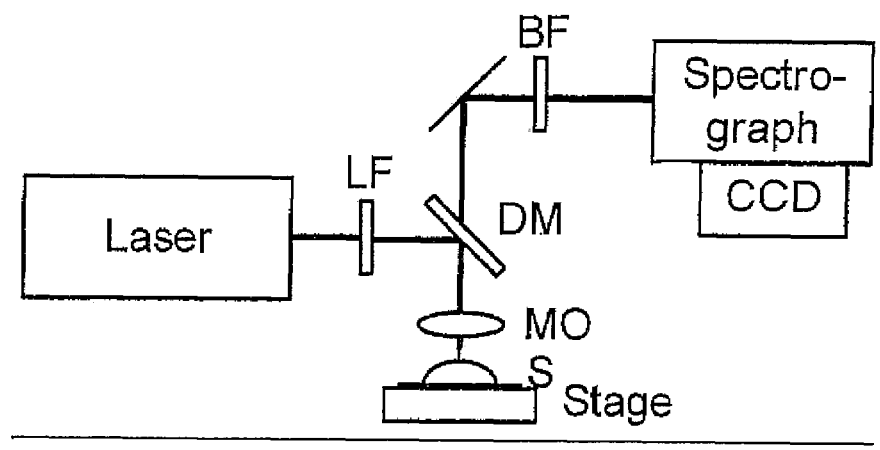
FIG. 1 illustrates a typical Raman spectrometer setup.

As used in the specification and claims, the singular forms "a", "an" and "the" include plural references unless the context clearly dictates otherwise. For example, the term "an array" may include a plurality of arrays unless the context clearly dictates otherwise.

An "array," "macroarray" or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray could generally contain spot sizes of less than 300 microns.

"Solid support," "support," and "substrate" refer to a material or group of materials having a rigid or semi-rigid surface or surfaces. In some aspects, at least one surface of the solid support could be substantially flat, although in some aspects it may be desirable to physically separate synthesis regions for different molecules with, for example, wells, raised regions, pins, etched trenches, or the like. In certain aspects, the solid support(s) could take the form of beads, resins, gels, microspheres, or other geometric configurations.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

The term "target" or "target molecule" refers to a molecule of interest that is to be analyzed, e.g., a nucleotide, an oligonucleotide, or a protein. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The term "molecule" generally refers to a macromolecule or polymer as described herein. However, arrays comprising single molecules, as opposed to macromolecules or polymers, are also within the scope of the embodiments of the invention.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which could be apparent upon review of this disclosure.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

When the macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it could be recognized by those of skill that the minimum length of a polynucleotide desired for specific hybridization to a target polynucleotide could depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions could vary depending on the application and are selected in accordance with the general binding methods known in the art.

It is appreciated that the ability of two single stranded polynucleotides to hybridize could depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, could remain single-stranded. Conversely, at lower stringency, the probability of formation of a mismatched duplex is increased.

The appropriate stringency that could allow selection of a perfectly-matched duplex, compared to a duplex containing one or more mismatches (or that could allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "ligand receptor pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value could be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The term "specific binding" or "specific interaction" is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide hybridization interactions, and so forth.

The term "bi-functional linker group" refers to an organic chemical compound that has at least two chemical groups or moieties, such are, carboxyl group, amine group, thiol group, aldehyde group, epoxy group, that can be covalently modified specifically; the distance between these groups is equivalent to or greater than 5-carbon bonds.

The phrase "SERS active material," "SERS active particle," or "SERS cluster" refers to a material, a particle or a cluster of particles that produces a surface-enhanced Raman scattering effect. The SERS active material or particle generates surface enhanced Raman signal specific to the analyte molecules when the analyte-particle complexes are excited with a light source as compared to the Raman signal from the analyte alone in the absence of the SERS active material or SERS active particle. The enhanced Raman scattering effect provides a greatly enhanced Raman signal from Raman-active analyte molecules that have been adsorbed onto certain specially-prepared SERS active surfaces. The SERS active surface could be planar or curved. Typically, the SERS active surfaces are metal surfaces. Increases in the intensity of Raman signal could be in the order of $10^4$-$10^{14}$ for some systems. SERS active material or particle includes a variety of metals including coinage (Au, Ag, Cu), alkalis (Li, Na, K), Al, Pd and Pt. In the case of SERS active particle, the particle size of SERS active particles could range from 1 to 5000 nanometers, preferably in the range of 5 to 250 nanometers, more preferably in the range of 10 to 150 nanometers, and most preferably 40 to 80 nanometers.

The term "capture particle" refers to a particle that can capture an analyte. The capture particle could be a coinage metal nanoparticle with surface modification to allow strong physical and/or chemical adsorption of analyte molecules and to allow adhesion of "enhancer particles" by electrostatic attraction, through specific interaction using a linker such as antibody-antigen, DNA hybridization, etc. or through the analyte molecule.

The term "enhancer particle" refers to a SERS active particle with suitable surface modification, a linker or an analyte which combines with a capture particle to form an aggregate. In case the capture particle is positively charged, then a negatively charged SERS active particle can be used as an enhancer particle without a linker, and vise versa. In case the capture particle has an antigen or an antibody, then a SERS active particle having a complimentary linker, namely, an antibody or an antigen, could be used as an enhancer particle.

The term "tagged particle" refers a SERS active particle having one or more different Raman active labels attached to the SERS active particle by direct attachment or through a surface modification. A tagged particle has a linker that can link to another tagged particle via an analyte.

As used herein, the term "colloid" refers to nanometer size metal particles suspending in a liquid, usually an aqueous solution. In the methods of the invention, the colloidal particles are prepared by mixing metal cations and reducing agent in aqueous solution prior to heating. Typical metals contemplated for use in the practice of the invention include, for example, silver, gold, platinum, copper, and the like. A variety of reducing agents are contemplated for use in the practice of the invention, such as, for example, citrate, borohydride, ascorbic acid and the like. Sodium citrate is used in certain embodiments of the invention. Typically, the metal cations and reducing agent are each present in aqueous solution at a concentration of at least about 0.5 mM. After mixing the metal cations and reducing agent, the solution is heated for about 30 minutes. In some embodiments, the solution is heated for about 60 minutes. Typically, the solution is heated to about 95° C. In other embodiments, the solution is heated to about 100° C. Heating of the solution is accomplished in a variety of ways well known to those skilled in the art. In some embodiments, the heating is accomplished using a microwave oven, a convection oven, or a combination thereof. The methods for producing metallic colloids described herein are in contrast to prior methods wherein a boiling silver nitrate solution is titrated with a sodium citrate solution. This titration method can produce one batch of silver particles with adequate Raman enhancement to dAMP in about 10 attempts, and the other batches have low or no Raman activity at all. However, by employing the methods of the invention, an average SERS signal enhancement of 150% is observed relative to colloids prepared from the titration method.

The metallic colloids could be modified by attaching an organic molecule to the surface of the colloids. Organic molecules contemplated would typically be less than about 500 Dalton in molecular weight, and are bifunctional organic molecules. As used herein, a "bifunctional organic molecule" means that the organic molecule has a moiety that has an affinity for the metallic surface, and a moiety that has an affinity for a biomolecule. Such surface modified metallic colloids exhibit an increased ability to bind biomolecules, thereby resulting in an enhanced and reproducible SERS signal. The colloids can be used either individually, or as aggregates for binding certain biomolecules.

Organic molecules contemplated for use include molecules having any moiety that exhibits an affinity for the metals contemplated for use in the methods of the invention (i.e., silver, gold, platinum, copper, aluminum, and the like), and any moiety that exhibit affinities for biomolecules. For example, with regard to silver or gold affinity, in some embodiments, the organic molecule has a sulfur containing moiety, such as for example, thiol, disulfide, and the like. With regard to affinity for a biomolecule such as a polynucleotide, for example, the organic molecule has a carboxylic acid moiety. In certain embodiments, the organic molecule is thiomalic acid, L-cysteine diethyl ester, S-carboxymethyl-L-cysteine, cystamine, meso-2,3-dimercaptosuccinic acid, and the like. It is understood, however, that any organic molecule that meets the definition of a "bifunctional organic molecule", as described herein, is contemplated for use in the practice of the invention. It is also understood that the organic molecule may be attached to the metallic surface and the biomolecule either covalently, or non-covalently. Indeed, the term "affinity" is intended to encompass the entire spectrum of chemical bonding interactions.

This surface modification of metallic colloids provides certain advantages in SERS detection analyses. For example, the surfaces of the metallic colloids could be tailored to bind to a specific biomolecule or the surfaces can be tailored to differentiate among groups of proteins based on the side chains of the individual amino acid residues found in the protein.

The term "COIN" refers to a composite-organic-inorganic nanoparticle(s). The COIN could be surface-enhanced Raman scattering (SERS, also referred to as surface-enhanced Raman spectroscopy)-active nanoclusters incorporated into a gel matrix and used in certain other analyte separation techniques described herein.

COINs are composite organic-inorganic nanoclusters. The clusters include several fused or aggregated metal particles with a Raman-active organic compound adsorbed on the metal particles and/or in the junctions of the metal particles. Organic Raman labels can be incorporated into the coalescing metal particles to form stable clusters and produce intrinsically enhanced Raman scattering signals. The interaction between the organic Raman label molecules and the metal colloids has mutual benefits. Besides serving as signal sources, the organic molecules promote and stabilize metal particle association that is in favor of SERS. On the other hand, the metal particles provide spaces to hold and stabilize Raman label molecules, especially in the cluster junctions.

These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanoparticle. The COINs can further comprise an organic layer overlying the metal layer, which organic layer comprises the probe. Suitable probes for attachment to the surface of the SERS-active nanoclusters include, without limitation, antibodies, antigens, polynucleotides, oligonucleotides, receptors, ligands, and the like.

The metal required for achieving a suitable SERS signal is inherent in the COIN, and a wide variety of Raman-active organic compounds can be incorporated into the particle. Indeed, a large number of unique Raman signatures can be created by employing nanoclusters containing Raman-active organic compounds of different structures, mixtures, and ratios. Thus, the methods described herein employing COINs are useful for the simultaneous detection of many multiple components such as analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoclusters described herein as COINs. This situation results in increased sensitivity compared to Raman-techniques that do not utilize COINs.

COINs could be prepared using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs could be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. COINs of different sizes can be enriched by centrifugation.

Typically, organic compounds are attached to a layer of a second metal in COINs by covalently attaching organic compounds to the surface of the metal layer Covalent attachment of an organic layer to the metallic layer can be achieved in a variety ways well known to those skilled in the art, such as, for example, through thiol-metal bonds. In alternative embodiments, the organic molecules attached to the metal layer can be crosslinked to form a molecular network.

The COIN(s) can include cores containing magnetic materials, such as, for example, iron oxides, and the like such that the COIN is a magnetic COIN. Magnetic COINs can be handled without centrifugation using commonly available magnetic particle handling systems. Indeed, magnetism can be used as a mechanism for separating biological targets attached to magnetic COIN particles tagged with particular biological probes.

The term "reporter" means a detectable moiety. The reporter can be detected, for example, by Raman spectroscopy. Generally, the reporter and any molecule linked to the reporter can be detected without a second binding reaction. The reporter can be COIN (composite-organic-inorganic nanoparticle), magnetic-COIN, quantum dots, and other Raman or fluorescent tags, for example.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxyletramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

When "fluorescent compounds" are incorporated into COINs, the fluorescent compounds can include, but are not limited to, dyes, intrinsically fluorescent proteins, lanthanide phosphors, and the like. Dyes useful for incorporation into COINs include, for example, rhodamine and derivatives, such as Texas Red, ROX (6-carboxy-X-rhodamine), rhodamine-NHS, and TAMRA (5/6-carboxyletramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromotrimethyl-ammoniobimane.

Multiplex testing of a complex sample could generally be based on a coding system that possesses identifiers for a large number of reactants in the sample. The primary variable that determines the achievable numbers of identifiers in currently known coding systems is, however, the physical dimension. Tagging techniques, based on surface-enhanced Raman scattering (SERS) of fluorescent dyes, could be used in the embodiments of this invention for developing chemical structure-based coding systems.

Multiplex testing of a complex sample would generally be based on a coding system that possesses identifiers for a large number of reactants in the sample. The primary variable that determines the achievable numbers of identifiers in currently known coding systems is, however, the physical dimension. Techniques, based on surface-enhanced Raman scattering (SERS) of organic compounds, could be used in the embodiments of this invention for developing chemical structure-based coding systems. The organic compound-assisted metal fusion (OCAM) method could be used to produce composite organic-inorganic nanoparticles (COIN) that are highly effective in generating SERS signals allows synthesis of COIN labels from a wide range of organic compounds to produce sufficient distinguishable COIN Raman signatures to assay any complex biological sample. Thus COIN particles may be used as a coding system for multiplex and amplification-free detection of bioanalytes at near single molecule levels.

COIN particles generate intrinsic SERS signal without additional reagents. Using the OCAMF-based COIN synthesis chemistry, it is possible to generate a large number of different COIN signatures by mixing a limited number of Raman labels for use in multiplex assays in different ratios and combinations. In a simplified scenario, the Raman signature of a sample labeled with COIN particles may be characterized by three parameters: (a) peak position (designated as L), which depends on the chemical structure of Raman labels used and the number of available labels, (b) peak number (designated as M), which depends on the number of labels used together in a single COIN, and (c) peak height (designated as i), which depends on the ranges of relative peak intensity.

The total number of possible distinguishable Raman signatures (designated as T) may be calculated from the following equation:

$$T = \sum_{k=1}^{M} \frac{L!}{(L-k)!k!} P(i, k)$$

where $P(i, k)=i^k-i+1$, being the intensity multiplier which represents the number of distinct Raman spectra that may be generated by combining k (k=1 to M) labels for a given i value. The multiple organic compounds may be mixed in various combinations, numbers and ratios to make the multiple distinguishable Raman signatures. It has been shown that spectral signatures having closely positioned peaks (15 cm$^{-1}$) may be resolved visually. Theoretically, over a million of Raman signatures may be made within the Raman shift range of 500-2000 cm$^{-1}$ by incorporating multiple organic molecules into COIN as Raman labels using the OCAMF-based COIN synthesis chemistry.

Thus, OCAMF chemistry allows incorporation of a wide range of Raman labels into metal colloids to perform parallel synthesis of a large number of COIN labels with distinguishable Raman signatures in a matter of hours by mixing several organic Raman-active compounds of different structures, mixtures, and ratios for use in the invention methods described herein.

COINs may be used to detect the presence of a particular target analyte, for example, a nucleic acid, oligonucleotide, protein, enzyme, antibody or antigen. The nanoclusters may also be used to screen bioactive agents, i.e. drug candidates, for binding to a particular target or to detect agents like pollutants. Any analyte for which a probe moiety, such as a peptide, protein, oligonucleotide or aptamer, may be designed can be used in combination with the disclosed nanoclusters.

Also, SERS-active COINs that have an antibody as binding partner could be used to detect interaction of the Raman-active antibody labeled constructs with antigens either in solution or on a solid support. It could be understood that such immunoassays can be performed using known methods such as are used, for example, in ELISA assays, Western blotting, or protein arrays, utilizing a SERS-active COIN having an antibody as the probe and acting as either a primary or a secondary antibody, in place of a primary or secondary antibody labeled with an enzyme or a radioactive compound. In another example, a SERS-active COIN is attached to an enzyme probe for use in detecting interaction of the enzyme with a substrate.

Another group of exemplary methods could use the SERS-active COINs to detect a target nucleic acid. Such a method is useful, for example, for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art. The oligonucleotide is then used to functionalize a SERS-active COIN. Detection of the specific Raman label in the SERS-active COIN identifies the nucleotide sequence of the oligonucleotide probe, which in turn provides information regarding the nucleotide sequence of the target polynucleotide.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or indexes of refraction.

The term "dispersive spectrometer" refers to a spectrometer that generates spectra by optically dispersing the incoming radiation into its frequency or spectral components. Dispersive spectrometers can be further classified into two types: monochromators and spectrographs. A monochromator uses a single detector, narrow slit(s) (usually two, one at the entrance and another at the exit port), and a rotating dispersive element allowing the user to observe a selected range of wavelength. A spectrograph, on the other hand, uses an array of detector elements and a stationary dispersive element. In this case, the slit shown in the figure is removed, and spectral elements over a wide range of wavelengths are obtained at the same time, therefore providing faster measurements with a more expensive detection system.

The term "analyte" means any atom, chemical, molecule, compound, composition or aggregate of interest for detection and/or identification. Examples of analytes include, but are not limited to, an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product and/or contaminant. In certain embodiments of the invention, one or more analytes may be labeled with one or more Raman labels, as disclosed below. The sample such as an analyte in the embodiments of this invention could be in the form of solid, liquid or gas. The sample could be analyzed by the embodiments of the method and device of this invention when the sample is at room temperature and at lower than or higher than the room temperature.

The term "label" or "tag" is used to refer to any molecule, compound or composition that can be used to identify a sample such as an analyte to which the label is attached. In various embodiments of the invention, such attachment may be either covalent or non-covalent. In non-limiting examples, labels may be fluorescent, phosphorescent, luminescent, electroluminescent, chemiluminescent or any bulky group or may exhibit Raman or other spectroscopic characteristics.

A "Raman label" or "Raman tag" may be any organic or inorganic molecule, atom, complex or structure capable of producing a detectable Raman signal, including but not limited to synthetic molecules, dyes, naturally occurring pigments such as phycoerythrin, organic nanostructures such as $C_{60}$, buckyballs and carbon nanotubes, metal nanostructures such as gold or silver nanoparticles or nanoprisms and nanoscale semiconductors such as quantum dots. Numerous examples of Raman labels are disclosed below. A person of ordinary skill in the art could realize that such examples are not limiting, and that "Raman label" encompasses any organic or inorganic molecule, compound or structure known in the art that can be detected by Raman spectroscopy.

The term "fluid" used herein means an aggregate of matter that has the tendency to assume the shape of its container, for example a liquid or gas. Analytes in fluid form can include fluid suspensions and solutions of solid particle analytes.

Described are methods and apparatus that utilize a photomultiplier (PMT) set, a photodiode set, or a photodiode array, coupled with a set of filters to collect Raman signal from samples. Specifically, the use of a filter set coupled to a PMT set, or photodiode set or array, allow for the diction of signals from several different wavelengths simultaneously. The methods and apparatus allow for the high speed detection of Raman signals from a multiplexed assay.

One embodiment is a device including a plurality of photomultiplier tubes (PMT)s or photodiodes configured to detect Raman signals from a sample, and a plurality of filters having a corresponding PMT or photodiode. The filters are configured to provide a different wavelength of Raman signals to each PMT or photodiode.

Preferably, the sample includes composite-organic-inorganic-nanoparticles (COINs). Preferably, the COINs include gold, silver, platinum, copper, or aluminum. Preferably, the COINs include one or more compounds of adenine, 4-aminopyrazolo(3,4-d)pyrimidine, 2-fluoroadenine, N6-benzolyadenine, kinetin, dimethyl-allyl-amino-adenine, zeatin, bromoadenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

Preferably, the device includes 3 or more filters and 3 or more PMTs or photodiodes. Preferably, the Raman signals detected are within the wavenumbers of 500 cm−1 to 2500 cm−1. Preferably, the plurality of PMTs or photodiodes consist of a plurality of PMTs or consists of a plurality of photodiodes.

Another embodiment is a device including a photomultiplier tube (PMT) or photodiode configured to detect Raman signals from a sample, and a filter set including a plurality of filters configured to limit the Raman signals received by the PMT or photodiode.

Yet another embodiment is a method of detecting Raman signals. The method includes receiving Raman signals from a sample utilizing a plurality of photomultiplier tubes (PMT)s or photodiodes, wherein at least one PMT or photodiode provides a different Raman signal than at least one other PMT or photodiode. In one configuration, the Raman signals may be received from a PMT and not a photodiode. In another configuration, the Raman signals may be received from a photodiode and not a PMT. Preferably, the Raman signals are used to construct an image of the sample.

Another embodiment is a method of detecting an analyte. The method includes receiving Raman signals from an analyte utilizing a plurality of photomultiplier tubes (PMT)s or photodiodes, wherein at least one PMT or photodiode provides a different Raman signal than at least one other PMT or photodiode, and comparing the received Raman signals to known Raman signals to detect an analyte. Another embodiment is a method of selecting a filter set for detecting Raman signals. The method includes determining the Raman peaks produced by a sample, and selecting a filter set that provides Raman signals at the determined peaks. Preferably, the filter set comprises a plurality of filters. Preferably, each filter has a bandwidth of less ±2 nm or less. Preferably, each filter has a bandwidth of less ±1 nm or less.

As described above, COIN particles are capable of providing a very strong Raman signal due to the selection of Raman active compounds and their geometry. In addition, it is possible to generate a large number of different Raman signatures by mixing Raman labels in different ratios and combinations to produce the COINs. These Raman signatures can be used as a kind of "barcode" to identify samples labeled with the COIN particles.

The Raman signature of a sample labeled with COIN particles may be characterized by three peak parameters: (a) peak position (designated as L), which depends on the chemical structure of Raman labels used and the number of available labels, (b) peak number (designated as M), which depends on the number of labels used together in a single COIN, and (c) peak height (designated as i), which depends on the ranges of relative peak intensity.

As previously described, typically, the Raman signatures of a sample have been obtained using a spectrometer including a CCD camera and a grating. The spectrometer provides the Raman spectrum of a sample all across a given wavelength. However, since a Raman signature can be identified from Raman information only at the peak positions, the spectrometer provides unnecessary Raman signal information by providing Raman signals non peek positions. Obtaining all of this information, only some of which is needed to identify the Raman signature, takes time. For example, utilizing the typical Raman spectrometer setup in FIG. 1, Raman signals from bioassays can be collected by a charge-coupled device (CCD) camera by scanning individual spots on a surface, for example, 400 spots in a 20×20 grid. Spectra data from these spots can be processed to generate an image based on Raman intensity. The speed of such scanning is typically about 200 ms per pixels.

It has been found that faster scanning times can be obtained by only obtaining Raman information at positions that correspond to possible peak positions of COIN particles that are being utilized to label a sample.

Photomultiplier Tubes (PMT) are light detectors that are useful in low intensity applications such as fluorescence spectroscopy. Due to high internal gain, PMTs are very sensitive detectors. They include a photocathode and a series of dynodes in an evacuated glass enclosure. Photons that strikes the photoemissive cathode emits electrons due to the photoelectric effect. Instead of collecting these electrons at an anode like in the phototubes, the electrons are accelerated towards a series of additional electrodes called dynodes. These electrodes are each maintained at a more positive potential. Additional electrons are generated at each dynode. This cascading typically effect creates 105 to 107 electrons for each photon hitting the first cathode depending on the number of dynodes and the accelerating voltage. This amplified signal is finally collected at the anode where it can be measured.

Photodiodes or photodiode arrays are also a preferred type of detector. A photodiode or a photodiode array converts impinging photons to an electrical signal. Hence, by measuring the output voltage or current from the photodiode or photodiode array, the intensity of the impinging light or photons can be determined. In this case, the intensity of the Raman scattered light can be estimated by the electrical signal from the photodiode or photodiode array.

The advantages to using a photodiode or photodiode array include compact size, simple driving circuits and high quantum efficiency. However, photodiode or photodiode arrays often suffer from higher noise levels.

In the past, the use of PMTs and photodiodes as Raman detectors have been limited because of the relatively weak Raman signal provided by Raman active labels. Accordingly, a single spectrum obtained in a wave-number scanning mode with high resolution would take a substantial amount of time. However, the use of a set of PMTs, or photodiodes, configured with a filter configured to detect Raman signals only at the peak locations of Raman labels in combination with Raman labels that possess a strong Raman intensity, particularly COINs, make it possible to collect Raman data using PMT and a filter set in a very short time.

Multiple PMT or photodiodes operating in combination constitute a PMT set or photodiode set. Preferably the PMT set or photodiode set also includes a filter set. The filter set limits each PMT or photodiode in the set to detecting a certain wavelength, which is different from other PMTs or photodiodes in the set. For example a PMT set may include two PMTs one with a window at 903 $cm^{-1}$ and one at 1666 $cm^{-1}$. The PMT set can then detect Raman signals at these two wavelengths simultaneously. Utilizing a set of PMT or photodiodes to detect Raman signals can improve the speed of Raman detection 1000 times or more.

Preferably, the filter set includes at 2 filters, more preferably at least 3 filters, even more preferably 3-20 filters. For fastest Raman detection, preferably, each filter has a corresponding PMT or photodiode. Alternatively, each PMT or photodiode may have two or more filters that it cycles through during a Raman scan.

Preferably, each filter has a wavelength window of 5 nm or less, more preferably 2 nm or less, most preferably 1 nm or less.

The filters can be made deposition of multi-layers of dielectric material. These filters can also be called interference filters because they utilize the interference caused by the dielectric layers. The wavelengths transmitted or reflected by the filter may be altered by changing the number of layers, the thickness of each layer, and the index of refraction of each layer. The customized interference filter can be obtained through optical coating companies, such as Chroma Technology Corp (Rockingham, Vt.) or Omega Optical (Brattleboro, Vt.).

Preferably, the filters are configured to transmit a wavelength band that is determined by the wavelength of Raman scattered light generated by the molecules of interest or by the label, such as COIN. The wavelength of the Raman scattered light is a function of the excitation laser and the wavenumber of the Raman band of the molecules of interest or of the label. When multiple chemicals or molecules of similar or overlapping Raman bands are present in the sample, a multivariate analysis can be performed to determine the number of transmission bands and the width and the peak position of each transmission band.

The stronger the Raman signal provided by the analytes the faster the PMT or photodiodes can provide a Raman signal of decent quality. Accordingly, preferably the Raman labels utilized provide a Raman peak intensity of at least 10 times of the peak intensity of methanol. More preferably, the Raman labels provide a peak intensity of at least 25 times of the peak intensity of methanol.

Figure 2:
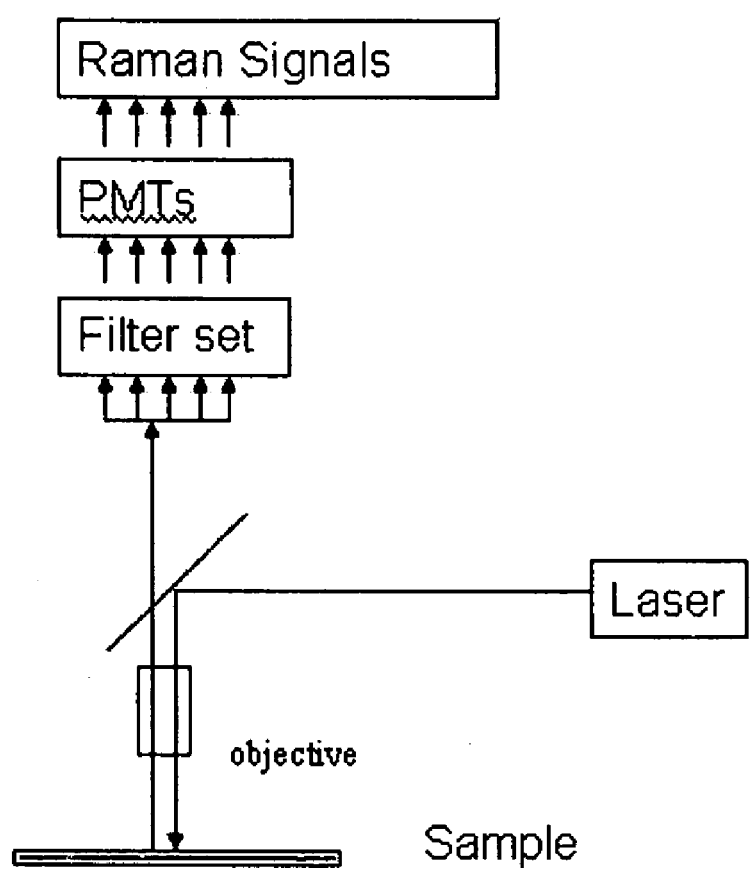
FIG. 2 shows an embodiment of a Raman detector using PMTs and a filter set.
Figure 3:
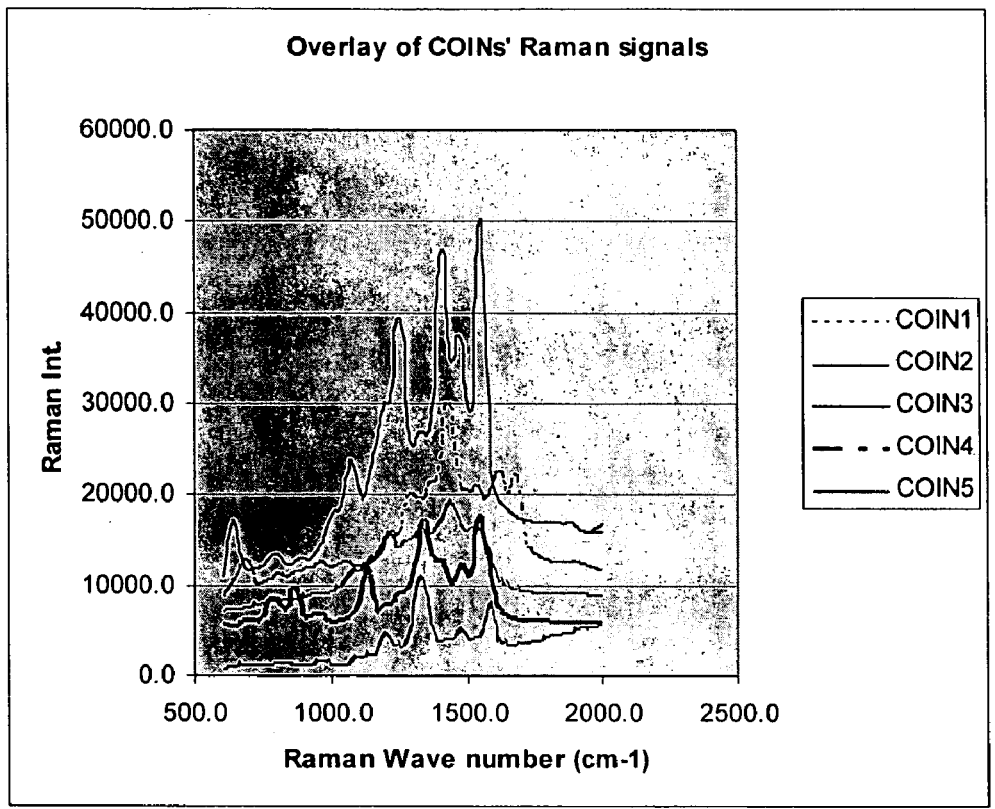
FIG. 3 shows the Raman signature for four types of Raman compounds.
Figure 3:
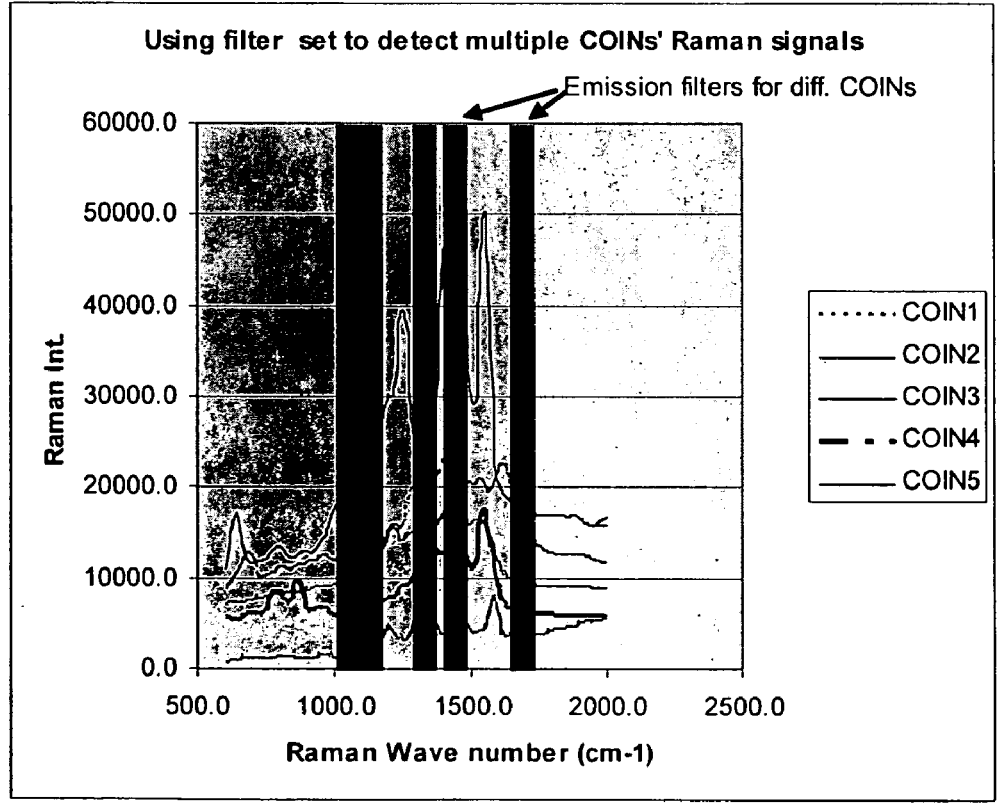

FIG. 2 shows an embodiment of a Raman detector using PMTs and a filter set. In this design, a PMT set replaces the CCD as the Raman signal detector. The filter set could include 3-20 filters, with wavelength window as narrow as 1 nm. FIG. 3 shows the Raman signature for four types of Raman compounds. As shown in FIG. 3 the Raman peaks for COINs are usually between 530 nm to 560 nm when a 514 nm laser is used as excitation source. Also, as shown in FIG. 3, preferably a filter set is configured to cover all the major Raman peaks of the COINs or other Raman labels utilized. Although using the filter set will give less spectra resolution compared to use a grating and a CCD camera, deconvolution of multiplexed signal is still feasible as Raman peaks of COIN are usually 2-5 nm wide, and each COIN has at least 2 major peaks.

The filter set is preferably designed based on the peak locations of the Raman labels that will be detected. For example, in a multiplexed assay involving 2 COINs (R6G and BFU), 2 filters with window centered in 903 cm−1 and 1666 cm−1 (536±1 nm and 559±1 nm if excitation laser's wavelength is 511 nm) could be applied, and the signal from these 2 filters would be characteristic for the 2 COINs. A similar detector using photodiode instead of PMT technology is also possible. Although photodiode typically provide lower sensitivity compared to PMTs in general, the sensitivity of an avalanche photodiode (APD) is comparable to PMT.

EXAMPLE

Figure 5A:
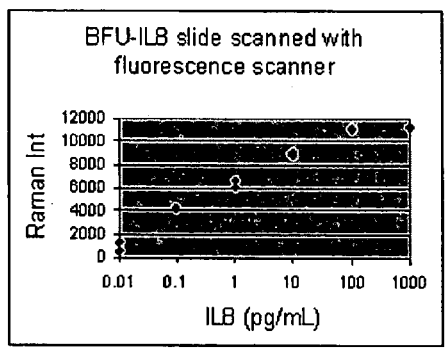
FIG. 5a shows the Raman signal from a PMT detector quantified by graphing the signal intensity against analyte concentration.
Figure 5B:
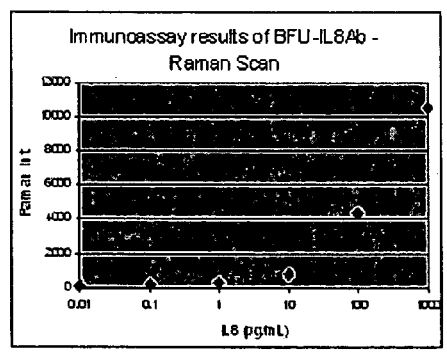
FIG. 5b shows the Raman intensity data from several scans that were averaged and the average peak height of specific Raman peak (1607 $cm^{-1}$) were plotted against corresponding analyte (IL8) concentrations.
Figure 6:
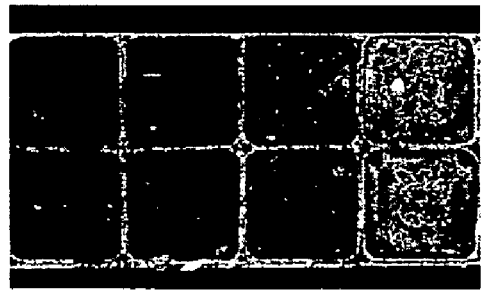
FIG. 6 shows an image of a sandwich assay with COIN labels performed using a 532 nm laser of an Axon scanner and detected using the "green" emission filter (545 nm -645 nm) and an image using a 635 nm laser and detected using a "red" filter (wavelength>690 nm).
Figure 6:
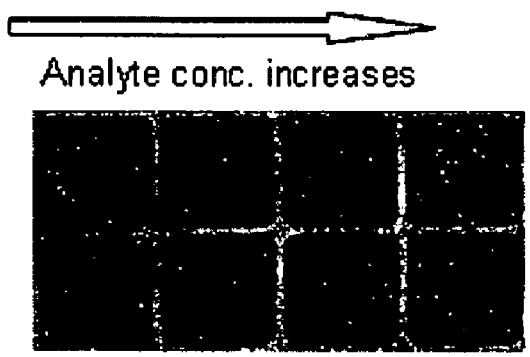

FIGS. 4-6 show that Raman signals from sandwich assays and reverse-phase assays using Raman labels (BFU and R6G COINs) can be detected with a commercially available florescence scanner (Axon microarray scanner 4200), which uses PMT as detector.

In FIGS. 4-6, sandwich assays with COIN Raman labels are performed using the following protocol:

The COIN particles were fabricated in accordance with the previously described methods.

Antibody-COIN conjugation: Carboxylic acid groups within BSA on the COIN surface were conjugated to free amine groups present in PSA antibodies. COIN-BSA nanoparticles were centrifuged and re-suspended in 10 mM borate buffer at pH 7.5. A vast excess of N-(3-Dimethylaminopropyl)-N'-ethylcarbodiimide (EDC) was added for 5 minutes and excess EDC was subsequently removed by centrifugation. An approximately 1000 fold excess of the IL8 antibody was reacted with the activated COIN surface for 40 minutes, washed 3 times to remove free antibody, and re-suspended in 10 mM borate, 1% BSA and 0.05% Tween-20. The final concentration of the COIN is in the range of 2-10 mM of Ag as determined by flame atomic-absorption spectroscopy (Shimadzu, Md., USA).

FIG. 4a illustrates how sandwich assays can be employed with COINs. In FIG. 4a, 16 wells on an aldehyde glass slide were isolated using FAST FRAME (Whatman, N.J., USA). These wells were used as substrates for immuno sandwich assays. To immobilize capture antibodies, 50 μL of an antibody (9 μg/mL) in 0.33×PBS was added to each well and the slide was incubated in an oven at 37° C. for 2 hours. After removing free antibodies, 50 μL of 1% BSA in a 10 mM glycine solution was added to each well to inactivate the aldehyde groups on the slide. The slide was incubated at 37° C. for another 1 hour before the wells were washed 4 times, each with 50 μL PBST washing solution (1×PBS, supplemented with 0.05% Tween-20).

Antigen binding and detection antibody binding (antibody-COIN conjugate binding) can be carried out following instructions from the antibody supplier (for example, BD biosciences). For example, after removing the unbound conjugates, the wells can be washed 4 times, each with 50 μL of washing solution. Finally, 30 μL of washing solution can be added to the wells before competitive binding. To demonstrate competitive binding, interleukin-2 protein (IL-2, 10 ng/mL) may be added to wells with anti-IL-2 capture antibody; anti-IL-2 antibody-coated COIN particles can be used to bind to the captured IL-2 molecules in the binding complexes. After washing the wells with buffer, samples containing different amounts of IL-2 can be added separately to the wells. The solutions containing released COINs from wells can be detected for COIN signals with a Raman scope.

Biomolecule analysis using Raman surface scanning: Generally, analyte (IL8) was diluted to standard solution of various concentrations, for example, 0, 0.1, 1, 10, 100, and 1000 pg/mL, in 1×PBS buffer containing 0.1% BSA and 0.05% Tween-20. These standard solutions are applied to the wells prepared above for immuno binding. After 2 hours, slides were rinsed twice with PBST, and then antibody-COIN conjugate solution was applied to each well. After 30 minute of antibody-COIN binding, slides were rinsed twice with PBST, and twice with water prior to Raman measurements.

The Raman measurement was performed using 2 methods:

FIG. 4b shows a COIN's Raman signal quantified by Raman scanning. The Raman signals were obtained using a Raman microscope built in-house. The beam from a 532 nm solid-state laser (Crystal Laser) is spatially filtered and expanded before it is reflected by a dichroic beam splitter (Chroma) and directed into a microscope (ME600L, Nikon) equipped with a 20× objective. The objective focuses the laser beam onto the sample and the back-scattered light is collected by passage through a holographic notch filter which attenuates the reflected laser excitation. A spectrometer and a thermoelectrically cooled charge-coupled device (CCD) camera record spectral data. Samples can be placed on a two-axis motorized stage and translated horizontally to achieve two-dimensional raster scans. Software was developed to automate the scanning and data acquisition. The integration time for each spectrum was 0.1 s. Raman intensity data from each scan was averaged and the average peak height of specific Raman peak (1607 cm$^{-1}$) were plotted against corresponding analyte (IL8) concentration in FIG. 5b.

In FIGS. 4c and 4d, Raman signal were obtained using a PMT-based Axon microarray scanner 4200. FIG. 4c shows that optical signal from a Raman peak can be selectively collected by applying an emission filter. FIG. 4d shows the raw signal from the Axon scanner. Note that the signal increases from left to the right side of the slides, corresponding to analyte (IL8) concentration increase.

In FIG. 5a, the Raman signal from a PMT detector is quantified by Axon scanner's data analysis software; and the signal intensity is plotted against analyte concentration. The linear intensity-analyte concentration relationship and the large detection range (0.1 pg/mL to 100 pg/mL) demonstrate that Raman detection is sensitive and quantitative.

In FIG. 6, the dual-laser excitation capability of Axon fluorescence scanner is exploited to show that the Raman signal can be detected using different excitation wavelengths (532 nm and 635 nm). In the upper image of FIG. 6, sandwich assay with COIN label is performed on a glass slide, and the slide is scanned using the 532 nm laser of the Axon scanner and detected using the "green" emission filter (545 nm-645 nm) and PMT. In the lower image of FIG. 6, the slide is scanned using the 635 nm laser and detected using "red" filter (collect photons with wavelength >690 nm) and PMT. Both images show that signal increases as the concentration of analyte increases from left side of the slide to the center. The ability to use multiple lasers to detect signal from one type of labels is an additional benefit as it enable users to adjust excitation resources according to their application needs.

The higher speed of a system equipped with filter set and PMT detector offers an advantage over sophisticate Raman scanner for detection involving only one Raman signal source. Using the Axon fluorescence scanner as an example, its scan speed is 1000 times faster than a Raman microscope (5 min for 1 Million pixels vs. 5 min for 1000 pixels), and the ability to use different excitation laser wavelength in such a system enables reduction of auto-fluorescence in tissue and cell-related imaging applications.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising:
   a plurality of photomultiplier tubes (PMT)s or photodiodes configured to detect Raman signals from a sample; and
   a plurality of filters having a corresponding PMT or photodiode and the filters are configured to provide a different wavelength of Raman signals to each PMT or photodiode,
   wherein the sample comprises composite-organic-inorganic-nanoparticles (COINs).

2. The device of claim 1, wherein the COINs comprise gold, silver, platinum, copper, or aluminum.

3. The device of claim 1, wherein the COINs comprise one or more compounds selected from the group consisting of adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

4. The device of claim 1, comprising 3 or more filters and 3 or more PMTs or photodiodes.

5. The device of claim 1, wherein the Raman signals detected are within the wavenumber of 500 cm$^{-1}$ to 2500 cm$^{-1}$.

6. The device of claim 1, wherein the plurality of PMTs or photodiodes consist of a plurality of PMTs.

7. The device of claim 1, wherein the plurality of PMTs or photodiodes consist of a plurality of photodiodes.

8. A device comprising:
   a photomultiplier tube (PMT) or photodiode configured to detect Raman signals from a sample; and
   a filter set comprising a plurality of filters configured to limit the Raman signals received by the PMT or photodiode,
   wherein the sample comprises Raman labels.

9. The device of claim 8, wherein the Raman labels are composite-organic-inorganic-nanoparticles (COINs).

10. The device of claim 8, wherein the COINs comprise one or more compounds selected from the group consisting of adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

11. The device of claim 8, comprising 3 or more filters.

12. The device of claim 8, wherein the Raman signals detected are within the wavenumber of 500 $Cm^{-1}$ to 2500 $cm^{-1}$.

13. The device of claim 8, wherein the PMT or photodiode consists of a PMT.

14. the device of claim 8, wherein the PMT or photodiode consists of a photodiode.

15. A method of detecting Raman signals comprising:
    receiving Raman signals from a sample utilizing a plurality of photomultiplier tubes (PMT)s or photodiodes, wherein at least one PMT or photodiode provides a different Raman signal than at least one other PMT or photodiode,
    wherein the sample comprises composite-organic-inorganic-nanoparticles (COINs).

16. The method of claim 15, wherein the COINs comprise gold, silver, platinum, copper, or aluminum.

17. The method of claim 15, wherein the COINs comprise one or more compounds selected from the group consisting of adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

18. The method of claim 15, wherein Raman signals are received from 3 or more PMTs or photodiodes.

19. The method of claim 15, wherein the Raman signals received are within the wavenumber of 500 $cm^{-1}$ to 2500 $cm^{-1}$.

20. The method of claim 15, wherein Raman signals are received from a PMT and not a photodiode.

21. The method of claim 15, wherein Raman signals are received from a photodiode and not a PMT.

22. A method of detecting an analyte comprising:
    receiving Raman signals from an analyte utilizing a plurality of photomultiplier tubes (PMT)s or photodiodes, wherein at least one PMT or photodiode provides a different Raman signal than at least one other PMT or photodiode; and
    comparing the received Raman signals to known Raman signals to detect an analyte,
    wherein the sample comprises composite-orclanic-inorclanic-nanoparticles (COINs).

23. The method of claim 22, wherein the COINs comprise gold, silver, platinum, copper, or aluminum.

24. The method of claim 22, wherein the COINs comprise one or more compounds selected from the group consisting of adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

25. The method of claim 22, wherein Raman signals are received from 3 or more PMTs or photodiodes.

26. The method of claim 22, wherein the Raman signals received are within wavenumber of 500 $cm^{-1}$ to 2500 $cm^{-1}$.

27. The method of claim 22, wherein Raman signals are received from a PMT and not a photodiode.

28. The method of claim 22, wherein Raman signals are received from a photodiode and not a PMT.

29. A method of selecting a filter set for detecting Raman signals comprising:
    determining the Raman peaks produced by a sample that produce best quantitative accuracy; and
    selecting a filter set that provides Raman signals at the determined peaks,
    wherein the filter set comprises a plurality of filters.

30. The method of claim 29, wherein each filter is connected to a photodiode or PMT.

31. The method of claim 29, wherein each filter has a bandwidth of ±1 nm.

32. The method of claim 29, wherein each filter has a bandwidth of ±2 nm.

33. The method of claim 29, wherein the sample comprises composite-organic-inorganic-nanoparticles (COINs).

34. The method of claim 33, wherein the COINs comprise gold, silver, platinum, copper, or aluminum.

35. The method of claim 33, wherein the COINs comprise one or more compounds selected from the group consisting of adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, rhodamine 6G, rhodamine B, crystal violet, basic fuchsin, cyanine 2, cyanine 3, and 9-amino-acridine.

36. The method of claim 29, the peaks are within wavenumber of 500 $cm^{-1}$ to 2500 $cm^{-1}$.

37. The method of claim 15, where the Raman signals are used to construct an image of the sample.

* * * * *